US006534294B1

(12) United States Patent
Lee et al.

(10) Patent No.: US 6,534,294 B1
(45) Date of Patent: Mar. 18, 2003

(54) PRODUCTION OF CHITOSAN-AND CHITIN-LIKE EXOPOLYMERS

(75) Inventors: Jin Woo Lee, Pusan (KR); Walter G. Yeomans, Framingham, MA (US); Alfred L. Allen, Pascoag, RI (US); Fang Deng, Drexel Hill, PA (US); Richard A. Gross, Plainview, NY (US); David L. Kaplan, Concord, MA (US)

(73) Assignees: Trustees of Tufts College, Medford, MA (US); University of Massachusetts Lowell, Lowell, MA (US)

( * ) Notice: Subject to any disclaimer, the term of this patent is extended or adjusted under 35 U.S.C. 154(b) by 0 days.

(21) Appl. No.: 09/723,657

(22) Filed: Nov. 28, 2000

Related U.S. Application Data

(63) Continuation of application No. PCT/US99/11723, filed on May 27, 1999.
(60) Provisional application No. 60/086,962, filed on May 28, 1998.

(51) Int. Cl.[7] .......................... C12P 19/04; C08B 15/00
(52) U.S. Cl. ...................... 435/101; 536/123; 536/56; 536/102; 536/112; 536/126
(58) Field of Search ........................ 435/101; 536/123, 536/56, 102, 112, 126

(56) References Cited

U.S. PATENT DOCUMENTS

| | | | | |
|---|---|---|---|---|
| 4,975,534 A | * | 12/1990 | Fox et al. | 536/123 |
| 5,232,842 A | | 8/1993 | Park et al. | 435/101 |
| 5,360,723 A | | 11/1994 | Hyatt et al. | 435/101 |
| 5,502,178 A | | 3/1996 | Gupta | 536/32 |
| 5,739,015 A | | 4/1998 | Srinivasan | 435/101 |

FOREIGN PATENT DOCUMENTS

| | | |
|---|---|---|
| JP | 07236495 | 9/1995 |
| JP | 07275698 | 10/1995 |

OTHER PUBLICATIONS

Kubota et al, Meiji Seika Kenkya Nenpo, 31:41–50, 1992.*
Anthonsen, M. W. et al., "Solution properties of chitosans: conformation and chain stiffness of chitosans with different degrees of N–acetylation," *Carbohydrate Polymers*, 22:193–201 (1993).
Arcidiacono, S. et al., "Molecular Weight Distribution of Chitosan Isolated from *Mucor rouxii* under Different Culture and Processing Conditions," *Biotechnology and Bioengineering*, 39:281–286 (1992).
Bartnicki–Garcia, S. et al., "Nutrition, Growth, and Morphogenesis of *Mucor Rouxii*," *J. Bacteriol.*, 84:841–858 (1962).
Canale–Parola, E. et al., "Synthesis of cellulose by *Sarcina ventriculi*," *Biochim. Biophys. Acta.*, 82:403–405 (1964).
Canale–Parola, E., "Biology of the Sugar–Fermenting Sarcinae," *Bacteriological Reviews*, 34(1):82–97 (1970).
Colvin, J. R. et al., "The structure of cellulose–producing bacteria, *Acetobacter xylinum* and *Acetobacter acetigenus*," *Can. J. Microbiol.*, 23:790–797 (1977).

Hackman, R. H. et al., "Light–Scattering and Infrared–Spectrophotometric Studies of Chitin an Chitin Derivatives," *Carbohydrate Research*, 38:35–45 (1974).
Kent, R. A. et al., "Bacterial Cellulose Fiber Provides an Alternative for Thickening and Coating," *Food Technology*, pp. 108 (1991).
Lee, J. W. et al., "Exopolymers from curdlan production: incorporation of glucose–related sugars by Agrobacterium sp. strain ATCC 31749," *Can. J. Microbiol.*, 43:149–156 (1997).
Legge, R. L., "Microbial Cellulose as a Speciality Chemical," *Biotech Adv.*, 258:303–319 (1990).
Matthysse, A. G. et al., "Genes Required for Cellulose Synthesis in *Agrobacterium tumefaciens*," *J. of Bacteriology*, 177(4):1069–1075 (1995).
Ogawa, R. et al., "Incorporation of GlcNAc residue into bacterial cellulose by *A. xylinum*—characterization of novel BC," *CELLULOSICS: Chemical, Biological and Material Aspects*, pp. 35–40 (1993).
Ogawa, R. et al., "Preparation of bacterial cellulose containing N–acetylglucosamine residues," *Carbohydrate Polymers*, 19:171–178 (1992).
Ogawa, R. et al., "Biosynthesis of Cellulose Susceptible for Chitinolytic Enzyme by Acetobacter SP," In *Adv. Chitin Chitosan*, Brine, C.J. et al., eds. (Proc. Int. Conf.), pp. 323–333 (1992).
Osawa, Z. et al., "Synthesis of sulfated derivatives of curdlan and their anti–HIV activity," Carbohydrate Polymers, 21:283–288 (1993).
Pinsent, C., "Getting There," *Open to the World*, pp. 26–30 (1997).
Roesser, D. S. et al., "Effects of Substitution Stie on Acetyl Amylose Biodegradability by Amylase Enzymes," *Macromolecules*, 29(1):1–9 (1996).
Ross, P. et al., "Cellulose Biosynthesis and Function in Bacteria," *Microbiological Reviews*, 55(1):35–58 (1991).
Schramm, M. et al, "Synthesis of Cellulose by *Acetobacter xylinum*," *Biochem J.*, 56:163–166 (1954).
Shirai, A. et al., "Preparation of a novel $(1{\rightarrow}4){-}\beta{-}D{-}$glycan by *Acetobacter xylinum*—a proposed mechanism for incorporation of a N–acetylglucosamine residue into bacterial cellulose," *Carbohydrate Polymers*, 32:223–227 (1997).
Shirai, A. et al., "Biosynthesis of a novel polysaccharide by *Acetobacter xylinum*," *Int. J. Biol. Macromol.*, 16(6):297–300 (1994).
White, S. A. et al., "Production and Isolation of Chitosan from *Mucor rouxii*," *Applied and Environmental Microbiol.*, 38(2):323–382 (1979).
Yamamoto, I. et al., "Synthesis, Structure and Antiviral Activity of Sulfates of Cellulose and its Branched Derivatives," *Carbohydrate Polymers*, 14:53–63 (1991).

* cited by examiner

*Primary Examiner*—Francisco Prats
(74) *Attorney, Agent, or Firm*—Hamilton, Brook, Smith & Reynolds, P.C.

(57) ABSTRACT

A method of producing biosynthetic copolymers comprising glucose and glucose analogs is provided. Glucose:glucose analog copolymers such as glucose:glucosamine, glucose:N-acetylglucosamine and glucose:glucosamine:N-acetylglucosamine are also provided.

4 Claims, 6 Drawing Sheets

PRODUCTION OF CHITOSAN-AND CHITIN-LIKE EXOPOLYMERS

RELATED APPLICATIONS

This application is a Continuation of PCT/US99/11723 filed May 27, 1999 which claims the benefit of U.S. Provisional Application No. 60/086,962, filed May 28, 1998, the entire teachings of which are incorporated herein by reference.

GOVERNMENT SUPPORT

The invention was supported, in whole or in part, by the United States Army. The Government has certain rights in the invention.

BACKGROUND OF THE INVENTION

Cellulose, (1–4)-linked-β-D-glucan, is a major structural component of the cell walls of higher plants (Delmer, D. P., and Amor, Y., *Plant Cell* 7:987–1000 (1995)). Some microorganisms also produce unbranched (1–4)-linked-β-D-glucan, named microbial cellulose (MC) (Schramm, M. and Hestrin, S., *Biochem. J.*, 56:163–166 (1954); Carr, J. G., *Nature* (London), 182:265–266 (1958) and Canale-Parola, E. and Wolfe, R. S., *Biochim. Biophys. Acta.* 82:403–405 (1964)). Cellulose is important industrially, for example, in the production of paper. Cellulose can be chemically detergents, varnishes, adhesives and for gelling or thickening of food stuffs or pharmaceuticals, depending on the extent of etherification.

Structurally related polysaccharides, such as chitin and chitosan, are also found in the biosphere. Chitin occurs as a major cuticular or skeletal component in all arthropods, in some invertebrates, and in the cell walls of some fungi. Chitin is a polysaccharide of high molecular weight and consists of unbranched chains of (1–4)-linked 2- acetamino-2-deoxy-β-D-glucose residues (Hackman, R. H. and Goldberg, M., *Carbohydr. Res.* 38:35–45 (1974)). Because of its abundance as a waste material from the canning food industry from crab, shrimp and lobster, chitin is an attractive starting material for the production of chitosan. Chitosan is the fully or partially deacetylated form of chitin (Anthosen, M. W., et al., *Carbohydr. Polym.* 22:193–201 (1993)). It contains β-(1–4)-linked 2-amino-2-deoxy-β-D-glucopyranose and 2-acetamido-2-deoxy-β-D-glucopyranose residues (Hirano, S., et al., *Carbohydr. Res.* 47:315–320(1976)). Chitosan is found in the cell walls of some fungi such as *Mucor rouxii* (Bartnicki-Garcia, S. and Nickerson, W. J., *J. Bacteriol.* 84:841–858 (1962)). However, like cellulose, chitin is generally insoluble in water and in most conventional solvent systems. Furthermore, the starting material, chitin, is easily degraded in the presence of acid.

Commercially, chitosan is derived by the chemical deacetylation of chitin from waste crustacean exoskeletons with strong alkali. This harsh conversion process, as well as variability in source material, leads to inconsistent physico-chemical characteristics (Arcidiacono, S. and Kaplan, D. L. *Biotechnol. Bioeng.*, 39:281–286 (1992).). The purification of chitosan derived from the cell wall of some fungi also requires strong alkaline treatment with heat, which leads to inconsistent material (White, S. A., et al., *Environ. Microbiol.*, 38:323–328 (1979); Arcidiacono, S. and Kaplan, D. L. *Biotechnol. Bioeng.*, 39:281–286 (1992)).

Glucose-rich polysaccharides such as cellulose and curdlan have been post-biosynthetically modified by nonspecific chemical means to change physical properties (Yamamoto, I. et al., *Carbohydr. Polym.*, 14:53–63 (1991); Osawa, Z., et al., *Carbohydr. Polym.*, 21:283–288 (1993)). For example, chemically modified cellulose and curdlan exhibited strong antiviral activity in vitro (Yamamoto, I. et al., *Carbohydr. Polym.*, 14:53–63 (1991); Osawa, Z. et al., *Carbohydr. Polym.*, 21:283–288 (1993)). Selective chemical modification of polysaccharides under homogeneous conditions also has been reported (Roesser, D. S. et al., *Macromol.*, 29:1–9 (1996)). However, it is extremely difficult to regiospecifically modify cellulose in the secondary hydroxyl position, to chemically generate glucosamine or N-acetylglucosamine, for example. Disadvantages of these synthetic approaches as well as purification of chitin from crustacean exoskeleton and plant and fungi cell walls include low yields, side reactions, the use of toxic solvents, and purification requirements.

Biosynthesis of polysaccharides has traditionally been studied using unmodified simple sugars such as glucose and sucrose, or complex carbon sources such as wheat gluten and molasses (Kaplan, D. L. et al., "Biosynthetic Polysaccharides In *Biomedical polymers: designed-to-degrade systems,*" edited by S. W. Shalaby, Hanser Publishers, New York. pp. 189–212 (1994)). Alternatively, microbial mutants have been used to manipulate biopolymer molecular weight, yield, and main chain or branch composition (Thorne, L., et al., *J. Bacteriol.* 169:3593–3600 (1987); Hassler, R. A. and Doherty, D. H., *Biotechnol. Prog.* 6:182–187 (1990)). Yet polysaccharides have not been well studied with respect to the incorporation of modified or non-native building blocks, unlike the extensive work with proteins for the incorporation of unnatural amino acids (Chung, H., et al., *Science* 259:806–809 (1993)), and bacterial polyesters with incorporation of a wide range of novel monomers (Brandl, H., et al., "Plastics from Bacteria and for Bacteria: Poly(β-Hydroxyalkanoates) as Natural, Biocompatible and Biodegradable Polyesters In *Advances in Biochemical Engineering/Biotechnology,*" Vol. 41, edited by T. K. Ghose and A. Fiechter. Springer, Berlin. pp.77 (1990); Steinbüchel, A., "Polyhydroxyalkanoic Acids In *Biomaterials: Novel Materials from Biological Sources,* edited by D. Byrom, Stockton Press, New York. pp. 123 (1991); Gross, R. A., "Bacterial Polyesters: Structural Variability in Microbial Synthesis In *Biomedical Polymers: Designed-to-Degrade Systems,* edited by S. W. Shalaby. Hanser Publishers, New York, pp. 173–188 (1994)).

Direct incorporation of glucose-related sugar monomers, 3-O-methyl-D-glucose (3-O-methylglucose) and 2-acetamido-2-deoxy-D-glucose (N-acetylglucosamine), into the main chain of biosynthesized curdlan has been reported (Lee, J. W. et al., *Can. J. Microbiol.* 43:149–156 (1997)). In related studies, direct incorporation of specific fatty acid pendent groups on a main chain polysaccharide such as emulsan has been demonstrated (Gorkovenko, A. et al., *Proc. Am. Chem. Soc. Div. Poly. Sci. Eng.*, 72:92–94 (1995); Gorkovenko, A. et al., *Can. J. Microbiol.*, 43:384–390 (1997); Zhang, J., et al., *Int. J. Biol. Macromol.*, 20:9–21 (1997)).

Bacterial cellulose containing a limited amount of N-acetylglucosamine has been described, however, the method to produce the copolymer required serial adapation of the bacteria in N-acetylglucosaime containing medium (Ogawa and Tokura, *Carbohydrate Polymers*, 19:171–178 (1992)). Furthermore, the copolymer produced only contained the glucose analog N-acetyglucosamine, at a mole percentage in liquid culture no greater than 4.5% (Ogawa and Tokura). Incorporation of up to 6.3% of N-acetylglucosamine has been achieved when bacteria were serially adapted to culture in N-acetylglucosamine and cultured in the presence of phosphorylated chitin (Shirai et al., *Int. J. Biol. Macromol.*, 16:297–300 (1994)).

Therefore, a method is needed to produce polysaccharides comprising useful glucose analogs such as glucosamine and N-acetylglucosamine that does not require harsh extraction protocols and such that variable levels of glucose analog incorporation can be achieved. Further, a method for the production of polysaccharides comprising glucose and glucose analogs other than N-acetylglucosamine is needed.

SUMMARY OF THE INVENTION

In the present invention, microbially produced polysaccharide copolymers are provided. Specifically, glucose analogs such as aminosugars are incorporated into polysaccharides produced as exopolymers (also referred to herein as copolymers or terpolymers) by *A. xylinum*. Examples of aminosugars are glucosamine and N-acetylglucosamine.

Polymer blends of cellulose-chitin and cellulose-chitosan have been reported; however, the availability of copolymers with the level of incorporation of these monomers as provided herein is novel and expected to result in new properties as well as enhanced control over structural features of the polysaccharide. Furthermore, the method of the present invention does not require adaptation of the polymer producing microbe to growth in glucose analog containing medium. Copolymers described herein possess new properties such as unique solubility behavior. In addition, direct formation of fibers by the bacteria are useful in the study of crystallinity and mechanical properties of the copolymers.

An advantage of bacterially produced cellulose and the copolymers of the present invention is that these molecules are produced by the bacteria in a commercially useful fiber form. Other sources of cellulose and chemically modified versions thereof require significant manipulation in order to generate the fiber form of the molecule. Furthermore, unlike other sources of cellulose, for example from plant and wood sources as well as other sources of chitin and chitosan, the microbially produced copolymers of the present invention are essentially pure polysaccharide. The copolymers of the present invention are easily purified to remove bacterial contaminants using methods well known in the art and as described herein.

The method to generate novel copolymers (cellulose-chitin, cellulose-chitosan) provided herein ameliorates the inherent difficulties associated with modifying plant-derived cellulose. In addition, this direct one-step process offers a simpler and less 'environmentally-damaging' approach than purification and modification of chitin (in terms of organic solvents, heavy metals, catalyst) towards new useful degradable polymers. Additional benefits for these fibrils are facile coupling chemistries that can be used to functionalize the amine groups in the cellulose-chitosan cellulose:chitin or cellulose:chitin:chitosan copolymers. These copolymers are useful for cross-linking, coupling of dyes or pharmaceuticals, or other surface treatments. In addition, chitin and chitosan are useful as relating agents (Muzzarelli, R. A. A., Chitin pp. 207–253, Pergamon Press, New York (1977)), drug carriers (Nakatsuka, S. and Andrady, A. L., *J. Appl. Polym. Sci.*, 44:17–28 (1992)), membranes (Blair, H. S. et al., *J. Appl. Polym. Sci.*, 33:641–656 (1987)), water treatment additives (Asano, T., "Chitosan Applications in Wastewater Sludge Treatment," In: *Proceedings of the First International Conference on Chitin/Chitosan*, R. A. A. Muzzarelli and E. R. Pariser (eds). pp231–252, MIT, Cambridge, Mass., USA (1978)), and wound-healing agents (Austin, P. R. et al., *Science*, 212:749–753 (1981); Minami, S. et al., *Carbohydr. Polym.*, 29:295–299 (1996)). Furthermore, the potential to incorporate blocks of chitin and chitosan into cellulose as described herein, provides new opportunities for cellulose-derived biomaterials, since the polymers now may be susceptible to lysozyme in the human body.

The present invention is drawn to a method for producing polysaccharide copolymers such as glucose:glucose analog polymers using a biosynthetic agent. The method of the present invention results in production of copolymers wherein the glucose analog is present in said polymer at a mole percent of at least about 1 to about 90 percent.

The present invention is further drawn to polysaccharide copolymers such as glucose:glucose analog polymers comprising glucosamine and glucose wherein glucosamine is present at a mole percent of at least about 1 to about 90 percent. The present invention is further drawn to glucose:glucose analog polymers comprising N-acetylglucosamine and glucose wherein N-acetylglucosamine is present at a mole percent of at least about 7 to about 90 percent. The present invention is further drawn to glucose:glucose analog polymers comprising glucosamine, N-acetylglucosamine and glucose, wherein the glucose analogs are present in the copolymer at a mole percent of at least about 1 to about 90 percent. The formation of chitin-like and chitosan-like polymers by direct bacterial incorporation of N-acetylglucosamine and glucosamine, respectively, as described herein provides new options in the synthesis and purification of consistent materials. This process results in more consistent polymer structural features, such as consistent levels of glucosamine or N-acetylglucosamine incorporation. In addition, the option to control monomer composition within the cellulose-chitin, cellulose-chitosan or cellulose-chitin-chitosan copolymers of the present invention provides new options in tailoring polymer functional properties such as solubility and reactivity. Novel combinations of properties can be envisioned by generating these types of copolymers, versus the individual homopolymer or traditional blends of two of the homopolymers.

Other cellulose-producing bacteria can be used in the method of the present invention. For example, other bacteria such as *Agrobacterium tumefaciens, Sarcina ventriculi*, or *Rhizobium leguminosarum* (trifolii) can be used in the method of the present invention. These other microbial sources of cellulose and cellulose:chitin or cellulose:chitosan copolymers are important because the ultrastructure of cellulose fibrils is different when generated from different bacteria. Ribbons and fibrils are formed by *A. xylinum*, while simple bundles and flocs are generated by *A. tumefaciens*. These differences may be important in the modulation of functional properties, degree of crystallinity. Also, *S. vertriculi*, as a Gram-positive cellulose-producing microorganism, generates cellulose that is closely associated with the cell wall and forms cell packets with a fibrillar structure. Furthermore, cellulose II (antiparallel arrangement of individual chains in crystalline cellulose, characteristic of industrially mercerized cellulose) is produced by *S. ventriculi*, while cellulose I (parallel arrangement of individual chains in crystalline cellulose) is formed by *A. xylinum* and *A. tumefaciens*. The ability to generate different copolymers in different chain configurations would be an additional benefit for the industrial and research use of the polymers.

The foregoing and other objects, features and advantages of the invention will be apparent from the following more particular description of preferred embodiments of the invention.

DETAILED DESCRIPTION OF THE INVENTION

The present invention is drawn to microbially produced exopolymers comprising glucose (cellulose) and glucose analogs and methods of producing and purifying said copolymers from cultures of cellulose producing bacteria such as *A. xylinum* ATCC 10245. Microbial cellulose is physically different from wood-derived cellulose. Viscometric determination of the weight average degree of polymerization (DPW) of MC is 2190 to 3470 (Legge, R. L., *Biotech. Adv.*, 258:303–319 (1990)). The very fine fiber structure of MC gives the fiber a surface area about 300 times greater than normal wood fiber (Kent, R. A. et al., *Food Technol.*, 108 (June 1991)).

Useful features of bacterial cellulose include a high degree of crystallinity, good mechanical strength of fibrils, high absorption capacity and chemical purity. The latter property results in substantially reduced processing requirements in comparison to cellulose derived from plant sources (Ross et al., *Microbiol. Reviews*, 55:35–38 (1991)). The mechanical properties of bacterial cellulose sheets are impressive, with Young's modulus >15 GPa (Yamanaka et al., *J. Materials Science*, 24:3141–3144 (1989)). The incorporation of the bacterial cellulose into paper results in improved paper strength.

Production of cellulose-chitin, cellulose-chitosan and cellulose-chitin-chitosan copolymers (also referred to herein as glucose:N-acetylglucosamine, glucose:glucosamine and glucose:N-acetylglucosamine:glucosamine, respectively) using glucose and glucose analogs as carbon sources are described herein and were confirmed by GC and GC/MS. In the method of the present invention, microbes produced exopolymers comprising glucose and glucose analogs such as 3-O-methylglucose, and 2-deoxy-D-glucose. In the method of the present invention, microbes produced exopolymers comprising glucose, glucosamine (chitosan) or N-acetylglucosamine (chitin). In the method of the present invention, microbes produced exopolymers comprising glucose glucosamine and N-acetylglucosamine. Thus, polymers containing at least two different monomers were synthesized by the method of the present invention. GC chromatograms of the fractionated exopolymers made with glucosamine or N-acetylglucosamine demonstrated that a mixture of polymers with different molar ratios of glucose to glucosamine or N-acetylglucosamine were produced. These polymers can be separated, for example, based on molar ratio of glucose to glucose analog using methods well known in the art. For example, solubility in the appropriate solvent, such as distilled water or 10% acetic acid can be used. The polymers can also be separated using standard separation techniques known in the art, techniques based, for example, on the size, molecular weight or charge of the polymer. Therefore, using the method of the present invention, a variety of glucose:glucose analog polymers, including glucose-co-glucosamine copolymers and glucose-co-N-acetylglucosamine copolymers with different contents of glucosamine and N-acetylglucosamine and different molecular weight can be generated.

As used herein, the term copolymer comprises a polymer of two or more different subunits and the term terpolymer comprises a polymer of three different subunits. Exopolymer refers to polymers of one or more different subunits produced microbially and present on the outside of the microbial cell.

The mole percent of glucose analog or analogs in the co-or terpolymer can be varied. For example, as shown in Table 3, the mole percent of glucosamine in a glucose:glucosamine copolymer was varied by varying the ratio of glucose-glucosamine in the medium. Other parameters to vary in order to vary the monomer content and size of the polymer are, for example, the speed at which the cultures are shaken, which can be from 0 to 300 rpm, depending on the microbe used and the pH of the medium, depending on the microbe used and the copolymer produced.

The present invention relates to glucose:glucose analog copolymers. In one embodiment of the present invention, a mole percent of glucose analog or analogs of about 1 to about 90% is achieved in the copolymer. In another embodiment of the present invention, the mole percent of glucosamine in the copolymer is about 5 to about 65%. In a more particular embodiment of the present invention, the mole percent of glucosamine in the copolymer is about 14 to about 65%. In still another embodiment, the mole percent of N-acetylglucosamine in the copolymer is about 7 to about 90%. In a more particular embodiment of the present invention, the mole percent of N-acetylglucosamine in the copolymer is about 14 to about 60%.

Glucosamine containing copolymers that are soluble in 10% acetic acid and copolymers that are insoluble in 10% acetic acid were generated using the method of the present invention. The acetic acid-insoluble glucose-co-glucosamine copolymer (AIGGCP) (the molar ratio of glucose to glucosamine in ASIGGCP was 6.0 to 1.0.) was also insoluble in distilled water (DW). The acetic acid-soluble glucose-co-glucosamine copolymer (ASGGCP) (the molar ratio of glucose to glucosamine in ASGGCP was 0.6 to 1.0.) showed the monomeric composition and solubility similar to chitosan, which is insoluble in DW, but soluble in acetic acid. N-acetylglucosamine containing copolymers that are soluble in DW and copolymers that are insoluble in DW were generated using the method of the present invention. The water-soluble glucose-co-N-acetylglucosamine copolymer (WSGGCP) (the molar ratio of glucose to glucosamine in WSGGCP was 0.8 to 1.0) was unexpected, and while not being bound by theory, may be soluble in DW under conditions such as high degree of acetylated exopolymer and low concentration of solute.

The present invention is also drawn to a method for producing polysaccharide copolymers such as glucose:glucose analog polymers using a biosynthetic agent. The method of the present invention results in production of copolymers wherein the glucose analog is present in said polymer at a mole percent of at least about 1 to about 90. In one embodiment of the method of the present invention, the glucose analog is selected from the group consisting of glucosamine, 3-O-methylglucose, N-acetylglucosamine, 2-deoxyglucose and combinations thereof. In another embodiment of the method of the present invention, the resulting copolymer comprises N-acetylglucosamine and glucosamine in addition to glucose. In one embodiment of the method, the mole percent of glucose analog or analogs in the copolymer is about 1 to about 90%. In another embodiment of the method, the mole percent of glucosamine in the copolymer is about 14 to about 65%. In another embodiment of the method, the mole percent of N-acetylglucosamine in the copolymer is about 7 to about 60%.

In one embodiment of the present invention, the biosynthetic agent is a microorganism. In a more specific embodiment, the microorganism is selected from the group consisting of: *Acetobacter xylinum, Agrobacter tumefaciens, Sarcina ventriculi, Rhizobium leguminosarum*, and *Acinetobacter calcoaceticus*.

For the copolymer production by *R. leguminosarum, S. ventriculi* and *A. tumefaciens*, growth is carried out under standard culture conditions, for these organisms, with the exception that the glucose analogs will also be fed as co-substrates or as sole substrates. *Rhizobium leguminosarum* bv. *Trifolii*, NAU 843 and NA 30 strains (Australian National University) will be grown in nutrient broth for routine culture or in defined media according to Napoli et al., *App. Microbiol.* 30:123–131 (1975) for the incorporation of glucose analogs. Cultures are incubated at 22° C. with 150 rpm rotary agitation. Flocculation is an indication of polysaccharide formation. Flocs of the bacterium are harvested by centrifugation at 16,000×g for 30 minutes and the polysaccharide such as cellulose or cellulose copolymer can be purified by acid hydrolysis to remove α-glucans or by any suitable means to remove the α-glucans without degrading the polysaccharide of interest. *S. ventriculi* (available from ATCC) is grown under anaerobic conditions on 2% glucose with or without glucose analogs and 2% yeast extract at 37° C. as described by Canale-Parola, *Bacteriological Reviews*, 34:82–97 (1970) and cellulose or cellulose polymer purified and characterized as described in the Exemplification. *A. tumefaciens* is grown on LB media at room temperature for 2–3 days with continuous shaking at 150–200 rpm (Matthysse et al., *J. Bacteriol*, 177:1069–1075 (1995)) in the presence of glucose and/or glucose analogs, as described and the cellulose or cellulose copolymer is purified as described below.

EXEMPLIFICATION

Microorganism

*Acetobacter xylinum* ATCC 10245 was obtained from the American Type Culture Collection (ATCC) and it is known to produce (1–4)-linked-β-D-glucan (microbial cellulose) (Colvin, J. R. and Sowden, L. C., *Can. J. Microbiol.* 23:790–797 (1977)). It was maintained on slants containing 2% glucose, 1.0% yeast extract, 1.0% Bacto-peptone, 4 mm $K_2HPO_4$, 86 mM $K_2HPO_4$, and 1.5% agar.

Chemicals

Glucose (>99.5% purity), 3-O-methyl-D-glucose, glucosamine (>99.0% purity), N-acetylglucosamine, 2-deoxy-D-glucose (2-deoxyglucose), and tertbutanol (>99.0% purity) were all purchased from Sigma Chemical Co. (St. Louis, Mo.). Methanol (>99.9% purity) was purchased from J. T. Baker Co. (Phillipsburg, N.J.); pyridine (>99.9% purity) was purchased from Aldrich Chemical Co. (Milwaukee, Wis.); acetic anhydride (>97.0% purity) and acetyl chloride (98% purity) were purchased from Fisher Scientific (Fair Lawn, N.J.); Tri-Sil Z (25% N-trimethylsilyimidazole in pyridine, v/v) for silylation was purchased from Pierce (Rockford, Ill.).

Growth Medium

The medium (Y3-3) for the production of cellulose was based on Johnson and Neogi (1989) and contained the following components (g/l): Peptone (Difco Bactopeptone), 10; yeast extract (Difco), 10; $K_2HPO_4$, 0.54; $K_2HPO_4$, 1.05; and 2% (w/v) carbon source. The carbon source was autoclaved separately for 20 min at 121° C. and added to the Y3-3 medium under aseptic conditions. Carbon sources included glucose and the following glucose analogs: 3-O-methylglucose, glucosamine, N-acetylglucosamine, and 2-deoxyglucose.

Production of Exopolymers

Starter cultures were prepared by transferring cells from agar slants to 50 ml of Y3-3 medium with 2% (w/v) glucose in 250 ml Erlenmeyer flasks. These cultures were incubated for 3 days at 30° C. and 50 rpm. This starter culture was used as a 5% (v/v) inoculum for 150 ml of Y3-3 medium with 2% carbon source in 500 ml Erlenmeyer flasks. Cultures were incubated for 7 to 14 days with either glucose or one of the glucose analogs under the same conditions as for the starter cultures.

Purification of Exopolymers

Figure 1:
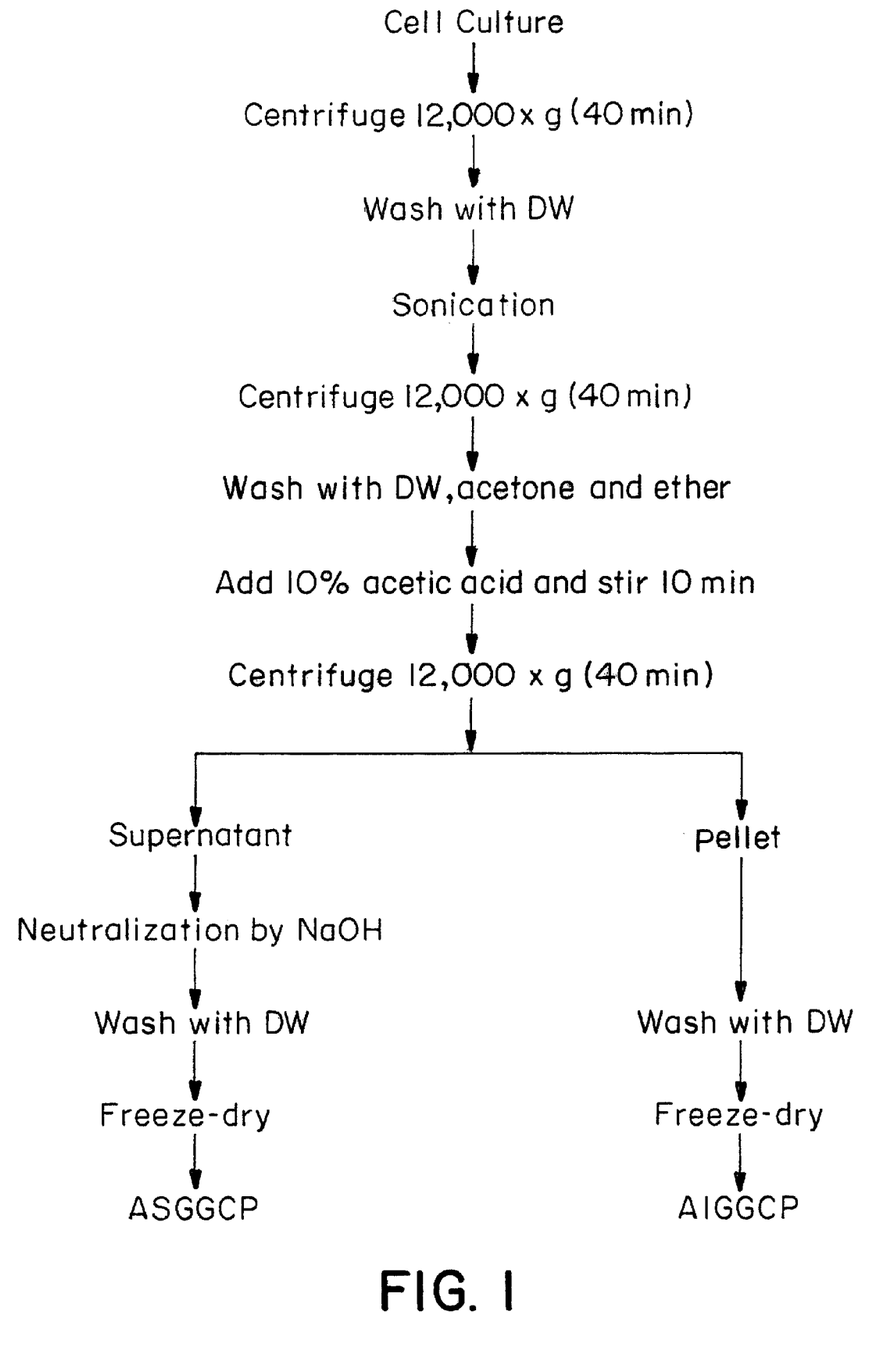
FIG. 1 is a flowchart of the simplified procedure to purify and fractionate microbially produced exopolymers synthesized with glucosamine, resulting in AIGGCT, (acetic acid insoluble glucose-co-glucosamine) copolymer and ASGGCP, (acetic acid-soluble glucose-co-glucosamine) copolymer.

Cell cultures of *A. xylinum* with the formed exopolymer were centrifuged at 12,000×g for 40 min at 4° C. (FIG. 1). After removing the supernatant, the precipitate was added to an equivalent volume of distilled water (DW) and the mixture was stirred for 10 min at room temperature. The resulting viscous solution was centrifuged at 12,000×g for 40 min at 4° C. After removing the supernatant, the precipitate was added to an equivalent volume of DW, the mixture was stirred for 10 min, and was sonicated for 5 min with the sonication level of 5 using a Cell Disruptor 350 (Branson Sonic Power Co., Danbury, Conn.) at room temperature. The resulting solution was centrifuged at 12,000×g for 40 min at 4° C. After removing the supernatant, the precipitate was added to an equivalent volume of DW and the mixture was stirred for 10 min. The resulting viscous solution was centrifuged at 12,000×g for 40 min at 4° C. After removing the supernatant, the precipitate was repeatedly washed with water, acetone, and ether. The washed precipitate was freeze-dried to obtain the total exopolymer produced by *A. xylinum* ATCC 10245.

Fractionation of Exopolymers Made with Glucosamine and N Acetylglucosamine

Further fractionation was accomplished by the addition of 150 ml of aqueous acetic acid (10%, v/v) to 300 mg of the exopolymer made with glucosamine. The resulting aqueous acetic acid solutions were centrifuged at 6,000×g for 20 min. The precipitate was washed with DW and freeze-dried. This fraction is termed exopolymer AmG-1 and represents the acetic acid insoluble glucose-co-glucosamine copolymer (AIGGCP). The supernatant was neutralized with sodium hydroxide and centrifuged at 15,000×g for 30 min. The precipitate was also washed with DW and freeze-dried. This fraction is termed exopolymer AmG-2 and represents the acetic acid-soluble glucose-co-glucosamine copolymer (ASGGCP).

Further fractionation was accomplished by addition of 450 ml of DW to 300 mg of the exopolymer made with N-acetylglucosamine. The resulting solutions were centrifuged at 6,000×g for 20 min. The precipitate was washed with DW and freeze-dried. This fraction is termed exopolymer AcG-1 and represents the water-insoluble glucose-co-N-acetylglucosamine copolymer (WIGGCP). The supernatant was dialyzed against deionized water using dialysis tubing with a molecular weight cut off of 3,000. After dialysis for 2–3 days with 4–5 changes of deionized water, the solution was freeze-dried. This fraction is termed exopolymer AcG-2 and represents the water-soluble glucose-co-glucosamine copolymer (WSGGCP).

Analytical Methods

The yield of the exopolymer by *A. xylinum* was determined by direct weighing after purification of exopolymers. Gas chromatographic analysis after methanolysis of exopolymers and subsequent trimethylsilylation was used to determine the composition of carbohydrates in the exopolymers (Chaplin, M., *Anal. Biochem.*, 123:336–341 (1982)). Samples (approximately 0.5 mg) were dried over phosphorous pentoxide, under vacuum, in 600 μl Reacti-Vials (Pierce, Rockford, Ill.). Methanolic hydrogen chloride (300 μl) prepared by mixing methanol and acetyl chloride in a ratio of 20 to 1 (v/v) was added and the tubes were sealed with teflon-lined septum caps. The contents were vortexed and heated at 70° C. for 24 hr with stirring. t-Butyl alcohol (30 μl) was then added to each tube before evaporating the contents using a stream of dry oxygen-free nitrogen at room temperature. For incubation on N-acetylglucosamine, complete N-acetylation of amino sugars was ensured by re-N-acetylation by addition of methanol (150 μl), pyridine (15 μl), and acetic anhydride (15 μl) to the above tubes. After standing at room temperature for 30 min, the solutions were evaporated to dryness by the use of a dry oxygen-free nitrogen stream at room temperature followed by vacuum over phosphorous pentoxide. After this thorough drying, Tri-Sil Z (100 μl) was added and each mixture was stirred for 2 hr at room temperature.

Gas chromatographic analyses were performed on a Hewlett Packard (HP) gas chromatograph, model 5890 Series II, equipped with a flame-ionization detector and HP model 7673 injector. The column was 30 m×0.32 mm I.D. fused silica with cross-linked 0.25 μm 5% phenylmethyl silicone liquid phase (Supelco, Pa.). Dry oxygen-free nitrogen (2.9 ml/min flow rate) was used as the carrier gas at 10 psi head pressure, using a temperature program (140° C. for 2 min, then increasing at 8° C. per min up to 260° C.). The injector was purged for 0.8 min after injection. To quantitate the repeat unit composition of products, response factors were generated from the relative values of GC peak areas using an equimolar mixture of pure sugars and m-inositol as the internal standard.

Gas chromatography/mass spectrometry (GC/MS) analyses were performed on a Hewlett Packard gas chromatograph, model 5890 Series II, also equipped with HP model 7673 injector and coupled to a Mass Selective Detector (HP 5971 Series). The capillary column was a cross-linked 5% pheryi methyl silicone fused silica (HP Ultra MS 5, 30 m×0.25 mm, film thickness 0.33 μl). Dry oxygen-free helium (0.8 ml/min flow rate) was used as the carrier gas, using a temperature program (140° C. for 2 min, then increasing at 8° C. per min up to 260° C.). Sample volumes of 1 μl were injected and the injector was surged for 0.6 min after injection.

Results

Effect of Glucose Analogs on the Production of Exopolymers

Glucose as the carbon source resulted in the highest production of exopolymer among the carbon sources used under the conditions of this experiment (Table 1). Both 3-O-methylglucose and 2-deoxyglucose as carbon source were not effectively utilized by *A. xylinum* ATCC 10245. There were some changes in pH of medium after 7 day cultures with different carbon sources. The yield of exopolymers purified from the culture with glucosamine and N-acetylglucosamine was not as high as with glucose, but higher than that obtained from either 3-O-methylglucose or 2-deoxyglucose.

TABLE 1

Production of Exopolymer with Glucose and its Analogs by *A. xylinum* ATCC 10245

| Carbon | pH[1] | Yield (mg/ml) | Conversion (%) |
|---|---|---|---|
| Glucose | 4.2 | 3.83 ± 0.45 | 19.1 |
| 3-O-Methylglucose | 5.3 | 0.21 ± 0.04 | 1.1 |
| Glucosamine | 4.5 | 0.37 ± 0.03 | 1.9 |
| N-Acetylglucosamine | 4.8 | 0.64 ± 0.07 | 3.2 |
| 2-Deoxyglucose | 5.2 | 0.16 ± 0.02 | 0.8 |

[1]The final pH (The initial medium pH was adjusted to between 5.1 and 5.2 prior to sterilization).

Structural Analysis of Fractionated Exopolymers Made with Glucosamine and N-acetylglucosamine To determine the repeat unit composition of exopolymers purified from cultures, samples were depolymerized and derivatized as described above and the GC patterns obtained were compared to carbohydrate standards (Chaplin, M., *Anal. Biochem.* 123:336–341 (1982)). The exopolymers made with glucosamine and N-acetylglucosamine were fractionated by acetic acid (10%, v/v) and DW, respectively (Table 2). GC chromatograms corresponding to exopolymer purified from cultures with glucose, glucosamine, acetic acid insoluble and soluble, and N-acetyl-glucosamine, DW insoluble and soluble are shown in FIGS. 2A through 2E, respectively. For all the products, the chromatograms show the major component to be glucose identified by the peak retention times and peak area ratios of the α and β anomers.

TABLE 2

Fractionation of Exopolymers made with Glucosamine by Acetic Acid (10%, v/v) and N-Acetylglucosamine by DW

| | | Insoluble Fraction | | Soluble Fraction | |
|---|---|---|---|---|---|
| Carbon[1] | Fractionation by | Amount[2] (%) | Molar Ratio[3] (Glu:AmG or Glu:AcG) | Amount (%) or Glu:AcG) | Molar Ratio (Glu:AmG) |
| Glucosamine | Acetic Acid | 90 | 6.0:1.0 | 10 | 0.6:1.0 |
| N-Acetylglucosamine | DW | 90 | 6.2:1.0 | 10 | 0.8:1.0 |

[1]The carbon source used for the production of exopolymer.
[2]Relative amount of insoluble and soluble fraction.
[3]Molar ratio of glucose to glucosamine or glucose to N-acetylglucosamine. The abbreviations used are as follows: glucose in Glu, glucosamine is AmGlu, and N-acetylglucosamine is N-AcGlu.

Initial GC identification of glucosamine found in the exopolymers purified from cultures with glucosamine and fractionated by acetic acid was based on the elution time of N-acetylglucosamine due to re-N-acetylation of aminosugars during sample preparation for GC (13.05 to 13.16, FIGS. 2B and 2C) (Chaplin, M., *Anal. Biochem.* 123:336–341 (1982)). Based on relative peak areas and response factors of corresponding standard sugars, the average molar percentage of glucosamine repeat units in the exopolymer made with glucosamine in this example was 19%. After fractionation of the glucosamine-incorporated exopolymer, the molar ratios of glucose to glucosamine in the acetic acid insoluble exopolymer (FIG. 2B) and that in the acetic-acid soluble exopolymer (FIG. 2C) were 6.0:1.0 and 0.6:1.0, respectively (the molar percentage of glucosamine in these exopolymers were 14% and 63%, respectively).

Terpolymers were also observed during the biosynthesis of modified cellulose fibrils through the incorporation of glucose analogs. *A. xylinum* cultures grown for 7 to 14 days with 2% carbon source comprising glucose and glucosamine. The bacterium was able to partially acetylate the glucosamine to form a polymer consisting of three monomers: glucose, glucosamine, and N-acetylglucosamine. Based on analysis methods described above, including GC/MS. The overall content of modified glucose analogs incorporated into the polymer in this example was as high as 19%. The content was divided between the glucosamine and N-acetylglucosamine.

Figure 2A:
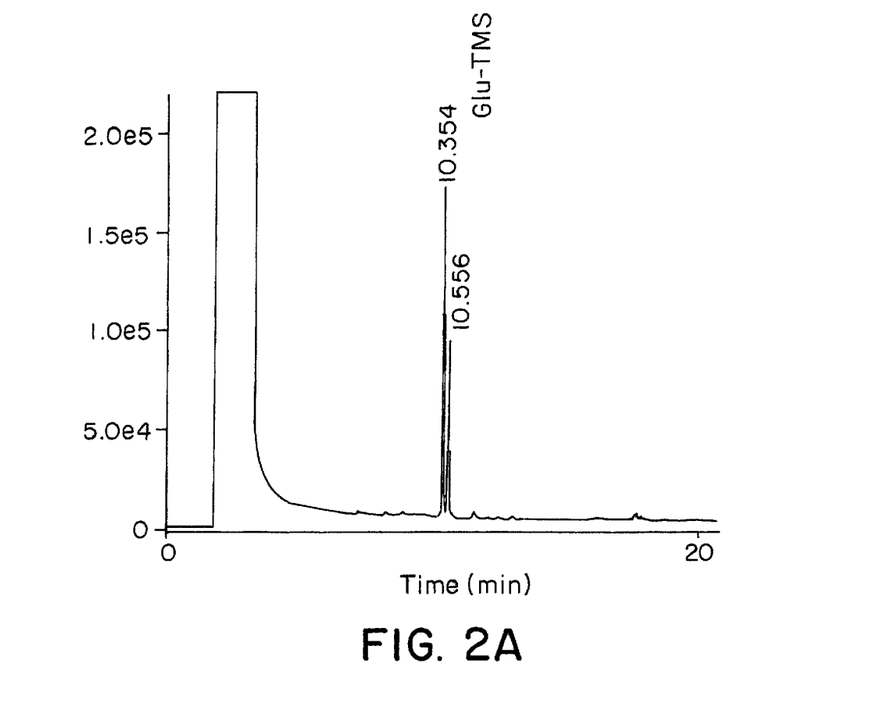
FIG. 2A is a gas chromatograph of trimethylsilylated (TMS) sugar components of exopolymer made with glucose.
Figure 2B:
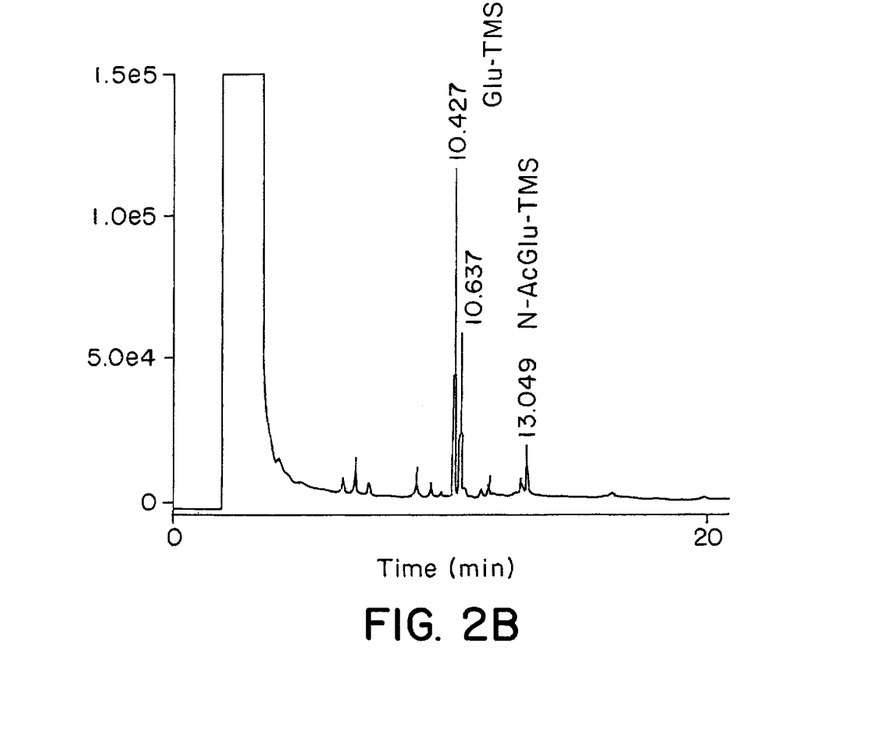
FIG. 2B is a gas chromatograph of TMS sugar components of 10% (v,v) acetic acid insoluble fraction of exopolymer made with glucosamine.
Figure 2C:
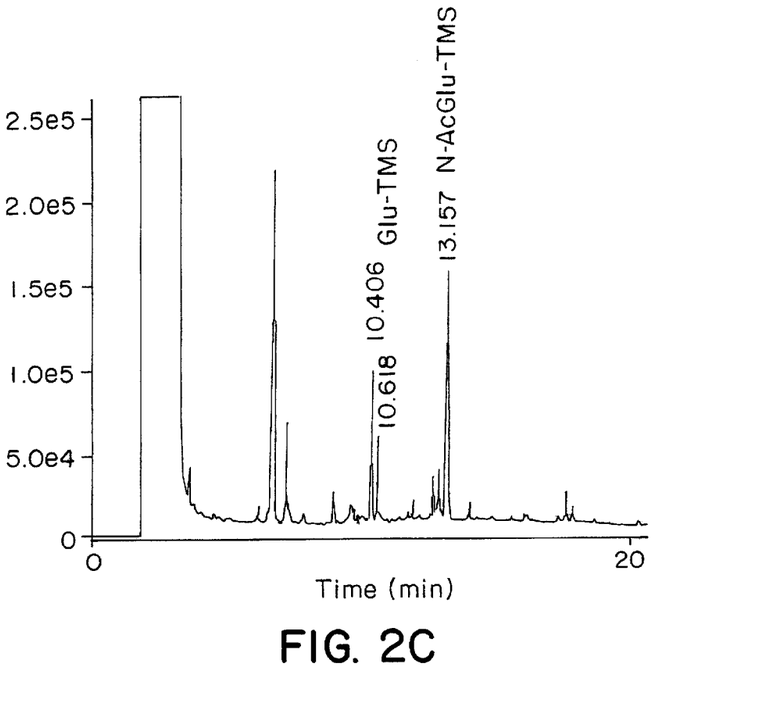
FIG. 2C is a gas chromatograph of TMS sugar components of 10% (v,v) acetic acid soluble fraction of exopolymer made with glucosamine.
Figure 2D:
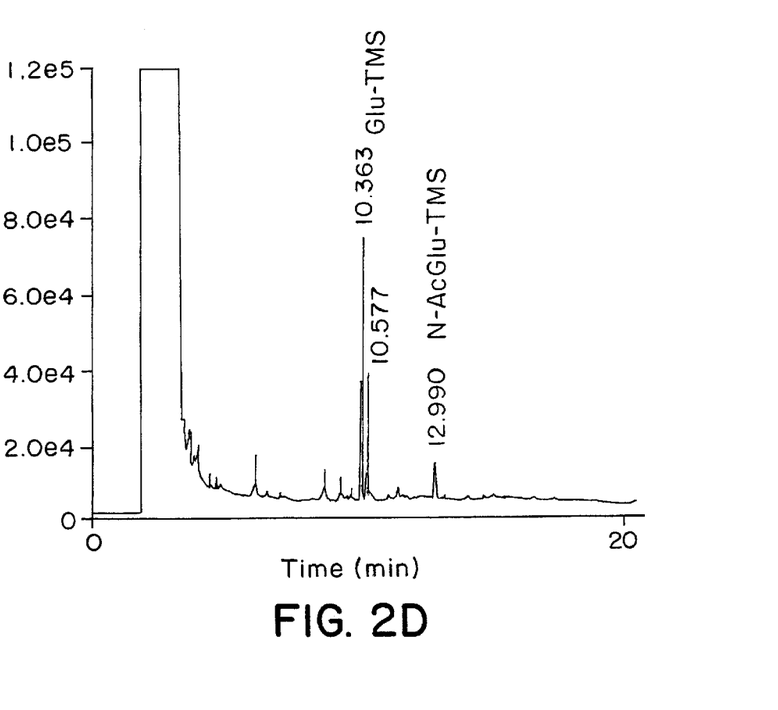
FIG. 2D is a gas chromatograph of TMS sugar components of water insoluble fraction of exopolymer made with N-acetylglucosamine.
Figure 2E:
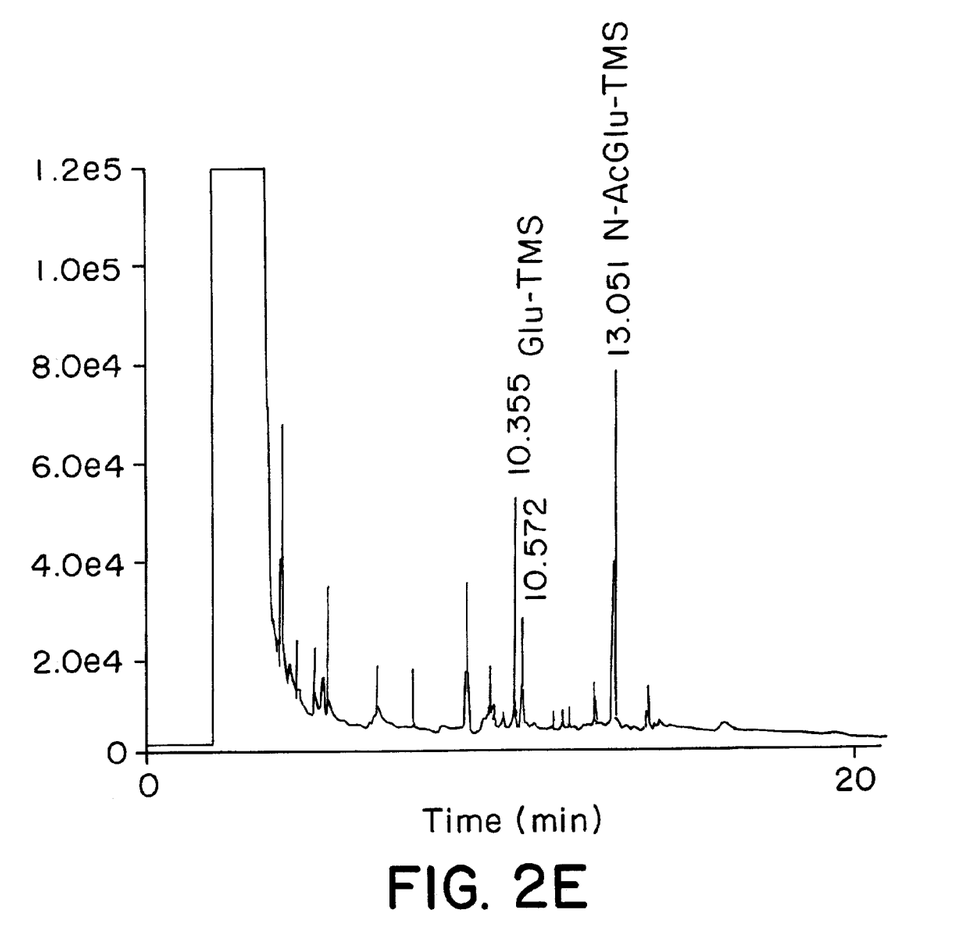
FIG. 2E is a gas chromatograph of TMS sugar components of water soluble fraction of exopolymer made with N acetylglucosamine.

GC identification of N-acetylglucosamine found in the exopolymers purified from cultures with N-acetylglucosamine and fractionated by DW was also based on the elution time (1 2.99 to 13.05) (FIGS. 2d and 2E). In this example, the average molar percentage of N-acetylglucosamine repeat units in the exopolymer made with N-acetylglucosamine was 18%. After fractionation of the N-acetylglucosamine-incorporated exopolymer by DW, the molar ratios of glucose to N-acetylglucosamine in the water insoluble exopolymer (FIG. 2d) and that in the water soluble exopolymer (FIG. 2E) were 6.2:1.0 and 0.8:1.0, respectively (the molar percentage of N-acetylglucosamine in these exopolymers were 14% and 56%, respectively).

Figure 3A:
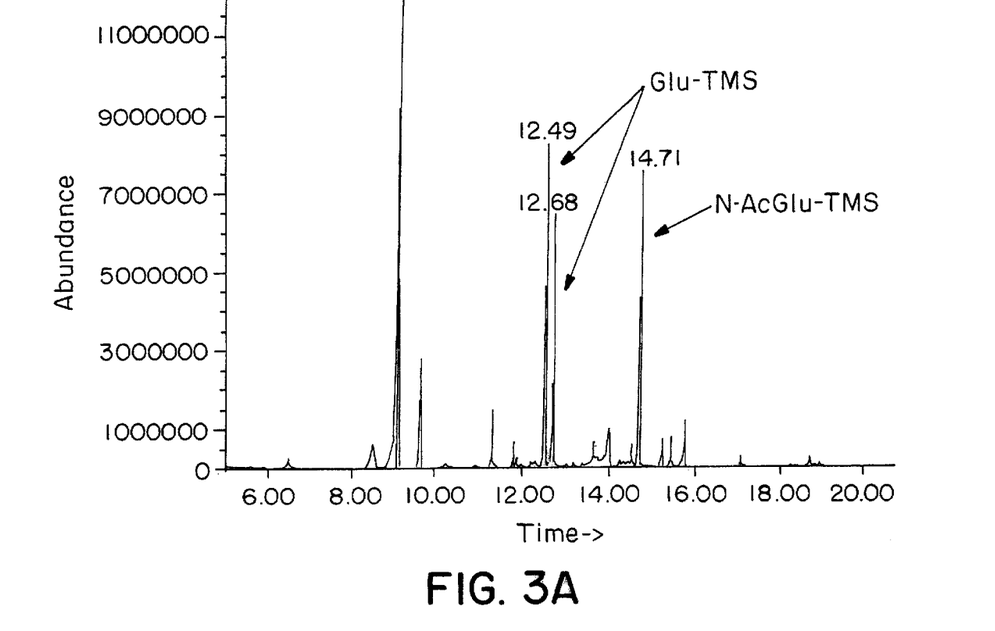
FIG. 3A show the results of gas chromatography/mass spectrometry (GC/MS) of TMS sugar components of 10% (v,v) acetic acid soluble fraction of exopolymer made with glucosamine.
Figure 3B:
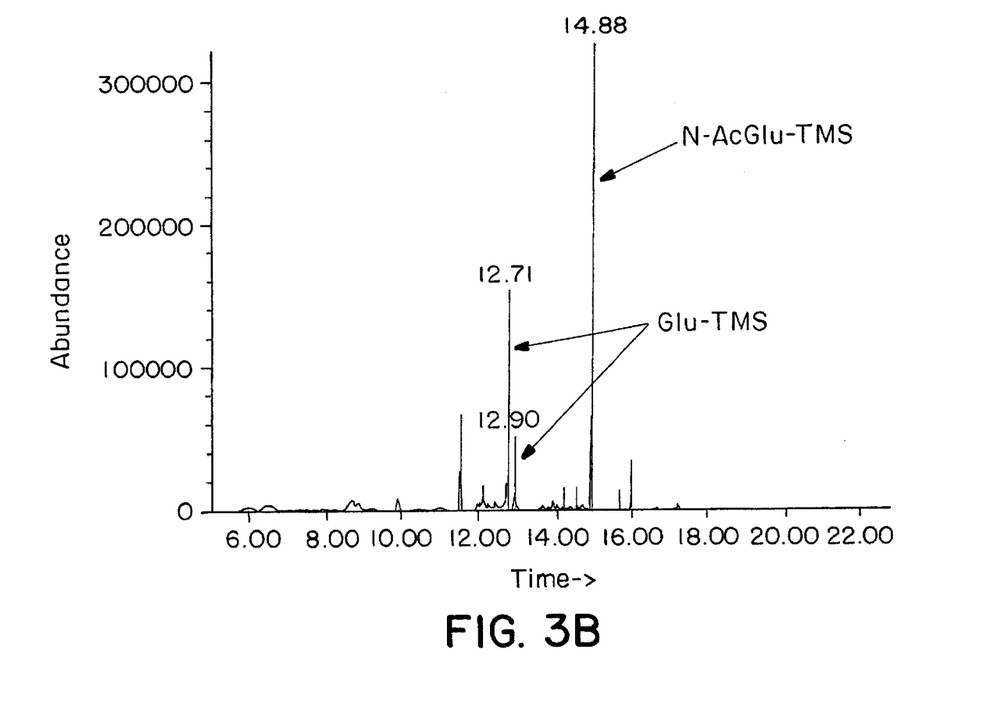
FIG. 3B are the results of GC/MS analysis of TMS sugar components of water soluble fraction of exopolymer made with N acetylglucosamine.

The presence of the trimethylsilyl (TMS) N-acetylglucosamine derivative in the GC/MS chromatogram of exopolymers with glucosamine and N-acetylglucosamine was confirmed by positive identification with reference spectra in the GC/MS data bank (FIGS. 3A and 3B).

Production of Exopolymers as a Function of Cultivation Time

Figure 4:
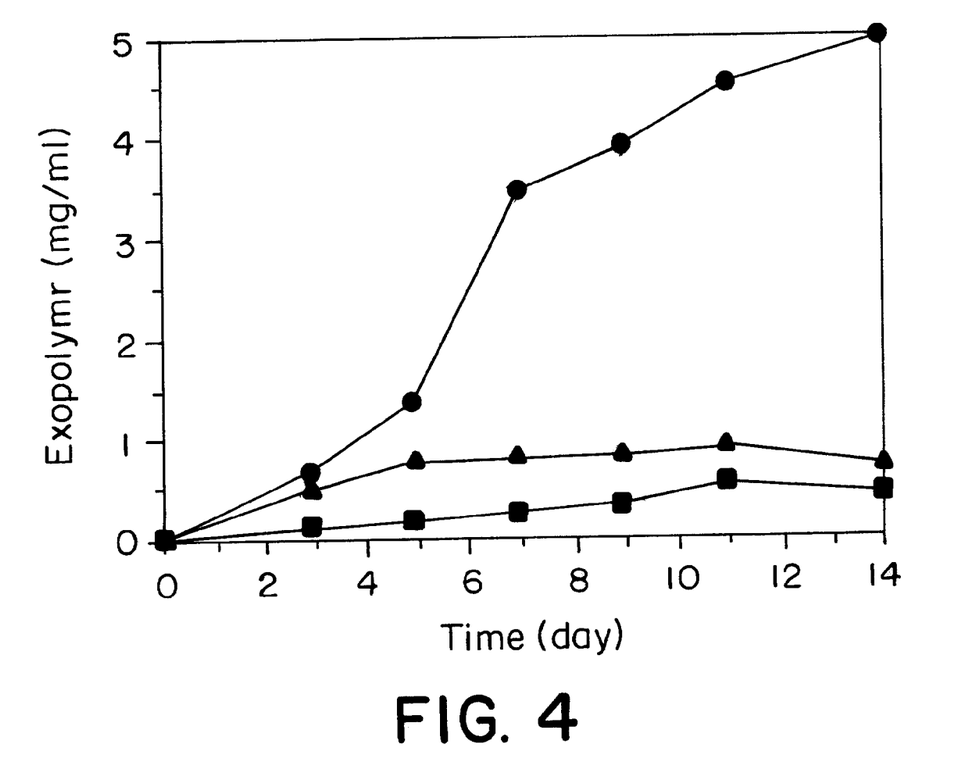
FIG. 4 is a chart showing the production of exopolymers with glucose (circles), glucosamine (squares), and N acetylglucosamine (triangles) as a function of cultivation time of *A. xylinum* ATCC 10245.

The production of exopolymers with glucose, glucosamine, and N-acetylglucosamine was observed as function of time up to 14 days (FIG. 4). The production of exopolymer with glucose steadily increased after 7 days and the conversion rate at 14 day reached at 4.98 mg/ml. The maximum yields made with glucosamine and N-acetylglucosamine were 0.50 mg/ml and 0.90 mg/ml after 11 day cultures, respectively. Unlike the culture with glucose as the carbon source, increase in cultivation time of *A. xylinum* with glucosamine or N-acetylglucosamine did not result in improvement of exopolymer production.

The effect of Co-substrate of Glucose and Glucosamine

To increase the production of glucosamine incorporated exopolymer; mixtures of glucose and glucosamine were used as carbon source (Table 3). The total concentration of mixed carbon sources was 2% (w/v). The higher the relative amount of glucose in the mixture, the higher the production of exopolymer, but the incorporation rate of glucosamine into exopolymer was lower. On the basis of GC analysis, the average incorporation rate of glucosamine in the exopolymer was 17% in this example and yield of exopolymer was 1.75 mg/ml when carbon source was the mixture of glucose (0.5%, v/v) and glucosamine (1.5%, v/v). The conversion rate to exopolymer was 8.8% on the basis of carbon source added.

TABLE 3

Production of Exopolymer with mixed Carbon of Glucose and Glucosamine by *A. xylinum* ATCC 10245[1]

| Carbon source (%) Glucose: Glucosamine | pH[2] | Yield (mg/ml) | Conversion[3] (%) | Incorporation[4] (%) |
|---|---|---|---|---|
| 2.0:0.0 | 4.16 | 3.80 ± 0.55 | 19.0 | 0.1 ± 0.2 |
| 1.5:0.5 | 4.10 | 3.20 ± 0.19 | 16.0 | 4.5 ± 0.2 |
| 1.0:1.0 | 4.10 | 2.47 ± 0.09 | 12.4 | 12.9 ± 0.4 |
| 0.5:1.5 | 4.10 | 1.60 ± 0.21 | 8.0 | 17.4 ± 1.3 |
| 0.0:2.0 | 4.04 | 0.34 ± 0.04 | 1.7 | 19.6 ± 2.2 |

[1]Results from 7 day cultures at 30° C. and values are the mean of triplicate experiments.
[2]The final pH (the initial medium pH was adjusted to 5.1–5.2 prior to sterilization.
[3]The conversion rate of exopolymer based on the carbon source added.
[4]The incorporation rate of glucosamine repeat unit into exopolymer.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A glucose:glucosamine copolymer wherein glucosamine is present at a mole percent in a range of between about 5 and about 65 percent.

2. A method for producing glucose:glucosamine copolymer comprising culturing a biosynthetic agent in medium comprising glucosamine, wherein glucosamine is present in said copolymer at a mole percent in a range of between about 5 and about 65 percent.

3. The method of claim 2, wherein the biosynthetic agent is a microorganism.

4. The method of claim 3 wherein the microorganism is selected from the group consisting of: *Acetobacter xylinum, Agrobacter tumefaciens, Sarcina ventriculi, Rhizobium leguminosarum, Mucor rouxii* and *Acinetobacter calcoaceticus.*

* * * * *

UNITED STATES PATENT AND TRADEMARK OFFICE
CERTIFICATE OF CORRECTION

PATENT NO. : 6,534,294 B1  
DATED : November 28, 2000  
INVENTOR(S) : Lee et al.

It is certified that error appears in the above-identified patent and that said Letters Patent is hereby corrected as shown below:

<u>Title page,</u>  
Item [73], add: -- Government of the United States/Department of the Army --

<u>Column 1,</u>  
Line 16, please insert before "BACKGROUND OF THE INVENTION"  
-- This invention was made with Government support under a contract awarded by the U.S. Army Soldier Systems Center, Natick, MA 01760. The Government has certain rights in the invention. --

Signed and Sealed this

Twenty-sixth Day of August, 2003

JAMES E. ROGAN  
*Director of the United States Patent and Trademark Office*